US010095271B2

(12) United States Patent  
Wang et al.

(10) Patent No.: US 10,095,271 B2  
(45) Date of Patent: Oct. 9, 2018

(54) MULTI-FACED DISPLAY DEVICE

(71) Applicants: BOE Technology Group Co., Ltd., Beijing (CN); Beijing Boe Optoelectronics Technology Co., Ltd., Beijing (CN)

(72) Inventors: Jiaheng Wang, Beijing (CN); Feng Bai, Beijing (CN); Jiuxia Yang, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 342 days.

(21) Appl. No.: 14/785,564

(22) PCT Filed: May 28, 2015

(86) PCT No.: PCT/CN2015/080098  
§ 371 (c)(1),  
(2) Date: Oct. 19, 2015

(87) PCT Pub. No.: WO2016/090861  
PCT Pub. Date: Jun. 16, 2016

(65) Prior Publication Data  
US 2017/0153669 A1 Jun. 1, 2017

(30) Foreign Application Priority Data  
Dec. 12, 2014 (CN) .......................... 2014 1 0773839

(51) Int. Cl.  
G06F 1/16 (2006.01)  
A61B 5/01 (2006.01)  
(Continued)

(52) U.S. Cl.  
CPC .......... *G06F 1/1647* (2013.01); *A61B 5/0075* (2013.01); *A61B 5/015* (2013.01);  
(Continued)

(58) Field of Classification Search  
CPC ..... G06F 1/1647; G06F 1/1652; A61B 5/015; A61B 5/0075; A61B 5/14532; A61B 5/7445; A61B 2562/06; A61B 2560/0462  
(Continued)

(56) References Cited

U.S. PATENT DOCUMENTS 7,387,422 B2 * 6/2008 Won .................... G02B 6/0036  
362/619  
2009/0082103 A1 3/2009 Lube  
(Continued)

FOREIGN PATENT DOCUMENTS

CN 1178917 A 4/1998  
CN 1558280 A 12/2004  
(Continued)

OTHER PUBLICATIONS

Office Action in Chinese Application No. 201410773839.9 dated Sep. 4, 2017, with English translation.  
(Continued)

*Primary Examiner* — Tuan T Dinh  
*Assistant Examiner* — Rockshana D Chowdhury  
(74) *Attorney, Agent, or Firm* — Womble Bond Dickinson (US) LLP

(57) ABSTRACT

A multi-faced display device includes a first display panel and a second display panel, each of which is curved to form an L-shaped structure. The first display panel is encapsulated with the second display panel such that the first display panel and the second display panel together form a closed structure.

19 Claims, 5 Drawing Sheets

(51) Int. Cl.
A61B 5/145 (2006.01)
A61B 5/00 (2006.01)

(52) U.S. Cl.
CPC ........ *A61B 5/14532* (2013.01); *A61B 5/7445* (2013.01); *G06F 1/1652* (2013.01); *A61B 2560/0462* (2013.01); *A61B 2562/06* (2013.01)

(58) Field of Classification Search
USPC .................................................... 361/679.01
See application file for complete search history.

(56) References Cited

U.S. PATENT DOCUMENTS

| | | | | |
|---|---|---|---|---|
| 2010/0117975 | A1* | 5/2010 | Cho | G06F 1/1626 345/173 |
| 2010/0253902 | A1 | 10/2010 | Yamazaki | |
| 2010/0277665 | A1* | 11/2010 | Kuo | G02F 1/13336 349/58 |
| 2013/0002572 | A1 | 1/2013 | Jin et al. | |
| 2013/0076612 | A1* | 3/2013 | Myers | G06F 1/1626 345/156 |
| 2013/0172068 | A1* | 7/2013 | Zhou | G06Q 30/02 463/16 |
| 2013/0235561 | A1* | 9/2013 | Etienne | G02F 1/133308 362/97.1 |
| 2013/0242230 | A1 | 9/2013 | Watanabe | |
| 2013/0271957 | A1* | 10/2013 | Etienne | G02F 1/133308 362/97.1 |
| 2013/0328792 | A1* | 12/2013 | Myers | G06F 1/1652 345/173 |
| 2014/0152646 | A1 | 6/2014 | Kang et al. | |
| 2014/0239065 | A1* | 8/2014 | Zhou | G06F 1/163 235/380 |

FOREIGN PATENT DOCUMENTS

| | | |
|---|---|---|
| CN | 201489227 | 5/2010 |
| CN | 101965604 A | 2/2011 |
| CN | 102855821 A | 1/2013 |
| CN | 103176304 | 6/2013 |
| CN | 103176304 A | 6/2013 |
| CN | 103955310 | 7/2014 |
| CN | 104035224 | 9/2014 |
| CN | 104407465 | 3/2015 |
| CN | 204241800 | 4/2015 |
| CN | 204241800 U | 4/2015 |
| EP | 2725474 | 4/2014 |
| KR | 20090089727 A | 8/2009 |

OTHER PUBLICATIONS

Office Action in Chinese Application No. 201410773839.9 dated Mar. 14, 2017, with English translation. 11 pages.
International Search Report and Written Opinion with English Language Translation, dated Aug. 26, 2015, Application No. PCT/CN2015/080098.
Office Action in Chinese Application No. 201410773839.9 dated Nov. 2, 2016, with English translation. 14 pages.
Internet article: http://china.nikkeibp.com.cn/news/auto/70896-201406091651.html, published Jun. 6, 2014, with English translation. 3 pages.
Internet article: http://china.nikkeibp.com.cn/news/flat/71297-201407081545.html, published Jul. 9, 2014, with English translation. 4 pages.
"Decision on Rejection," CN Application No. 201410773839.9 (dated Feb. 7, 2018).
"Partial Supplemental Search Report," EP Application No. 15790438.4 (dated Jun. 28, 2018).

* cited by examiner

MULTI-FACED DISPLAY DEVICE

CROSS-REFERENCE TO THE RELATED APPLICATIONS

The present application is the U.S. national phase entry of PCT/CN2015/080098, with an international filing date of May 28, 2015, which claims the benefit of Chinese Patent Application No. 201410773839.9, filed on Dec. 12, 2014, the entire disclosures of which are incorporated herein by reference.

FIELD OF THE DISCLOSURE

The present disclosure relates to the field of display technology, and particularly to a multi-faced display device.

BACKGROUND OF THE DISCLOSURE

As display devices are used in more fields, they have already not been limited to meet needs of planar display. Currently, there already occurs a design of a device capable of displaying on multiple faces. Such a multi-faced display device, for example, a lamp box, is generally formed by joining a plurality of planar display screens to perform display in respective directions. Such a multi-faced display device has edges at joining locations of respective display surfaces and cannot achieve continuity of images displayed in respective directions. In addition, in a context of ultra-slim design, due to a limited area of a lateral side, such a multi-faced display device cannot display specific information in a desired manner.

SUMMARY OF THE DISCLOSURE

In view of the above, embodiments of the present disclosure provide a multi-faced display device to achieve continuous display on multiple faces and display of specific information in a desired manner.

A multi-faced display device according to an embodiment of the present disclosure comprises a first display panel and a second display panel, wherein a lateral side of the first display panel curves toward a back side of a display region such that the first display panel forms an L-shaped structure, a lateral side of the second display panel curves towards a back side of a display region such that the second display panel forms an L-shaped structure, a lateral side of the first display panel opposite to the curved lateral side is encapsulated with the curved lateral side of the second display panel, and the curved lateral side of the first display panel is encapsulated with a lateral side of the second display panel opposite to the curved lateral side to form a closed structure, and a display surface of the multi-faced display device is an outside surface and/or inside surface of the closed structure.

In an optional implementation, the multi-faced display device further comprises a first encapsulating plate for sealing a top of the closed structure and a second encapsulating plate for sealing a bottom of the closed structure.

In an optional implementation, the first display panel and the second display panel, the first display panel and the first encapsulating plate, the first display panel and the second encapsulating plate, the second display panel and the first encapsulating plate, and the second display panel and the second encapsulating plate are assembled in a manner of press-fitting via a groove and a corresponding protrusion which are engaged with each other, of gluing, or of screwing.

In an optional implementation, the two lateral sides of the first display panel and second display panel are respectively encapsulated via a third encapsulating plate.

In an optional implementation, the third encapsulating plate, the first encapsulating plate and the second encapsulating plate are of an integral structure.

In an optional implementation, the multi-faced display device further comprises at least one function slot and/or physical function key, wherein the function slot and/or physical function key are disposed at an encapsulating location of the lateral sides of the first display panel and/or second display panel; or disposed at a non-display region of the first display panel and/or second display panel; or disposed on a surface of the first encapsulating plate and/or the second encapsulating plate.

In an optional implementation, the multi-faced display device further comprises a health monitoring unit configured to detect health information of a human body, wherein the health monitoring unit is disposed at an encapsulating location of the lateral sides of the first display panel and second display panel; or disposed at a non-display region of the first display panel and/or second display panel; or disposed on a surface of the first encapsulating plate and/or the second encapsulating plate.

In an optional implementation, the health monitoring unit is an infrared detecting unit and/or a minimal invasion detecting unit, the infrared detecting unit being configured to monitor a body temperature, the minimal invasion detecting unit being configured to monitor a blood sugar value.

In an optional implementation, the first display panel and second display panel comprise a main display surface and a non-main display surface, the non-main display surface being adapted to display health information detected by the health monitoring unit.

In an optional implementation, the first display panel and second display panel do not have a bezel at least at an encapsulating location of the lateral sides.

In an optional implementation, the first display panel and second display panel further comprise a circuit board, the circuit board of the first display panel and second display panel being connected to the display panels via a flexible electronic skin.

In an optional implementation, transparent prism structures for changing a direction of exit light are provided at least at an encapsulating location of lateral sides of the first display panel and second display panel.

In an optional implementation, the transparent prism structures at least partly protrude out of an outside surface of the closed structure, a cross section of the transparent prism structures perpendicular to the outside surface of the closed structure being in a semi-circular shape or an isosceles trapezoid shape.

In an optional implementation, the first display panel is a liquid crystal display panel, an organic electroluminescence display panel or an electronic paper display panel, and the second display panel is a liquid crystal display panel, an organic electroluminescence display panel or an electronic paper display panel.

In an optional implementation, the first display panel and second display panel are touch control display panels.

Advantageous effects of embodiments of the present disclosure include: as compared with a multi-faced display device formed by a plurality of planar display panels, the display device employing two L-shaped display panels achieves a curved display surface resulting from connection of arcuate surfaces, thereby enhancing continuity of images displayed in respective directions of the multi-faced display device and providing a capability of displaying specific information in a desired manner.

DETAILED DESCRIPTION OF THE DISCLOSURE

Figure 1:
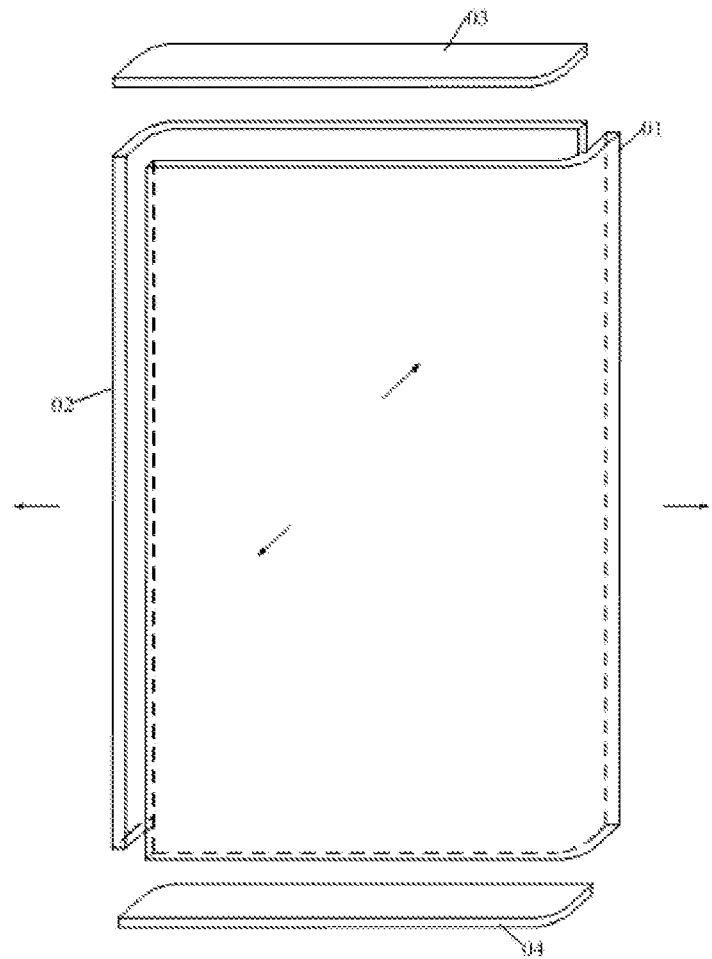
FIG. 1 is a first exploded view showing the structure of parts of a multi-faced display device according to an embodiment of the present disclosure.

A multi-faced display device provided by embodiments of the present disclosure is described in detail below with reference to the accompanying drawings. Shapes and sizes of parts shown in the drawings do not necessarily reflect a real proportion of the multi-faced display device and are only intended to illustrate the present disclosure.

As shown in FIG. 1, an embodiment of the present disclosure provides a multi-faced display device comprising a first display panel 01 and a second display panel 02. A lateral side of the first display panel 01 curves toward a back side of a display region such that the first display panel 01 forms an L-shaped structure. A lateral side of the second display panel 02 curves towards a back side of a display region such that the second display panel 02 forms an L-shaped structure. A lateral side of the first display panel 01 opposite to the curved lateral side is encapsulated with the curved lateral side of the second display panel 02, and the curved lateral side of the first display panel 01 is encapsulated with a lateral side of the second display panel 02 opposite to the curved lateral side to form a closed structure, as shown in a top view of FIG. 2.

Furthermore, the multi-faced display device further comprises a first encapsulating plate 03 for sealing a top of the closed structure and a second encapsulating plate 04 for sealing a bottom of the closed structure. The first encapsulating plate 03 and the second encapsulating plate 04 need to be arranged in a corresponding shape according to a cross-sectional shape of the closed structure so as to seal the top and bottom of the closed structure.

Figure 2:
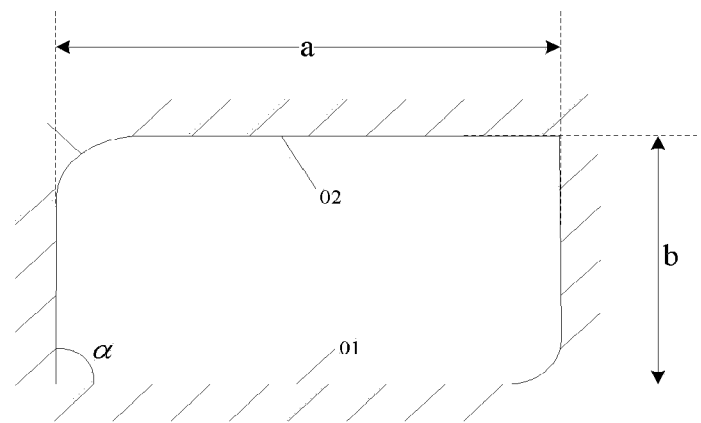
FIG. 2 is a top view of the multi-faced display device according to an embodiment of the present disclosure.

Display surfaces of the multi-faced display device may be outside surfaces of the closed structure, as shown by oblique lines in FIG. 2. Of course, in some applications of the display device, the display surfaces of the multi-faced display device may also be inside surfaces of the closed structure, or even both outside surfaces and inside surfaces may be arranged as the display surfaces. For example, in arrangement of an exhibition hall, an outer wall surface and/or inner wall surface of the whole exhibition hall may be arranged as display surfaces of the multi-faced display device.

Noticeably, as shown in FIG. 1, an obliquely upward arrow indicates a rear surface of the closed structure, an obliquely downward arrow indicates a front surface of the closed structure, a leftward arrow indicates a left lateral surface of the closed structure, and a rightward arrow indicates a right lateral surface of the closed structure.

As can be seen from FIGS. 1 and 2, the closed structure of the multi-faced display device comprises four straight surfaces and two arcuate surfaces, and the straight surfaces in at least four directions (front, rear, left and right) and the two arcuate surfaces of the closed structure all can perform a function of displaying images. As compared with a multi-faced display device formed by a plurality of planar display panels, the display device according to the present disclosure employs two L-shaped display panels to achieve arcuate connection of two groups of display panels in two directions (front and right, rear and left), thereby enhancing continuity of images displayed in respective directions of the multi-faced display device. In addition, as compared with a multi-faced display device with an arcuate surface for connection at each of four corners, the embodiment of the present disclosure trades off between continuity of displayed images and difficulty for manufacturing the display device. Because only one arcuate display surface needs to be processed for each of the first display panel 01 and the second display panel 02, the processing and assembling of the display device becomes easier.

Upon implementation, a proportion of lengths b and a of two adjacent straight surfaces of the multi-faced display device may be adjusted according to an application scenario of the multi-faced display device so that a profile of the multi-faced display device approximates a column-shaped structure having a rectangular cross section or a square cross section. When the multi-faced display device is applied to a mobile terminal such as a mobile phone, the front and rear surfaces may be arranged as having larger areas and left and right lateral surfaces be arranged narrower to facilitate an ultra-slim design of the mobile terminal. In this case, the display surface of the multi-faced display device is generally an outside surface of the closed structure. In addition, integral parts of the mobile terminal such as a power supply and a circuit board may be mounted inside the closed structure of the multi-faced display device so that the outer surface of the mobile terminal forms a whole on which images may be displayed. When the multi-faced display device is applied to for example a 3D display wall for 3D multi-face display, the front and rear surfaces and left and right lateral surfaces may be set as having substantially the same area. In this case, the display surface of the multi-faced display device may be the outside surface and/or inside surface of the closed structure.

Additionally, an angle α between the two adjacent straight surfaces of the multi-faced display device may be adjusted as needed. Generally, to achieve excellent continuity of images displayed on respective display surfaces of the multi-faced display device, the angle α is generally selected as an obtuse or right angle. FIG. 2 exemplarily illustrates that the angle α is a right angle.

Upon implementation, at least one display surface of the multi-faced display device may be set as a main display surface according to the application scenario of the multi-faced display device. For example, when the multi-faced display device is applied to a mobile terminal such as a mobile phone, the front surface of the first display panel 01 and the rear surface of the second display panel 02 may be used as main display surfaces. In this case, a working state of the multi-faced display device may be set in the following several types:

1. The two main display surfaces display the same content simultaneously, e.g., the front surface and rear surface may display the same image simultaneously;

2. The two main display surfaces display different content respectively, e.g., the front surface displays an image of a front side of a human body whilst the rear surface displays an image of a back side of the human body;

3. Only one of the main display surfaces displays content while other display surfaces are in an OFF state;

4. A plurality of non-main display surfaces (e.g., a left lateral surface, a right lateral surface, a curved transition surface joining the left lateral surface to the rear surface, and/or a curved transition surface joining the right lateral surface and the front surface) display the same content simultaneously;

5. The plurality of non-main display surfaces display different content respectively; and 6. Only one of the plurality of non-main display surfaces displays content while other display surfaces are in an OFF state.

Furthermore, the plurality of non-main display surfaces may be combined into a single entire non-main display surface. For instance, the left lateral surface and the curved transition surface joining the left lateral surface to the rear surface may be combined into a single display surface, and the right lateral surface and the curved transition surface joining the right lateral surface to the front surface may be combined into a single display surface.

Some UI icons for function keys, APPs or the like may be displayed on the non-main display surfaces according to arrangement. For example, function buttons may be displayed on the left lateral surface, right lateral surface, the curved transition surface joining the left lateral surface to the rear surface, or the curved transition surface joining the right lateral surface and the front surface. Specific information such as information associated with personal attributes of the user may also be displayed on the non-main display surfaces (discussed below).

Arrangement and working states of the main display surfaces and non-main display surfaces are described only by way of example, and not limitation. Upon implementation, the first display panel 01 and the second display panel 02 may, as a whole, display the same content, or display different content in regions.

Upon implementation, the first display panel 01 and second display panel 02 of the multi-faced display device may be made from a touch control display panel such that it is convenient for the user to directly perform corresponding operations with the touch control display panel when the function buttons are displayed. Of course, the first display panel 01 and second display panel 02 may also be non-touch control display panels, which is not limited here.

In particular, when the multi-faced display device is applied to a display wall, the first display panel and second display panel may also be produced as transparent display panels. As such, some articles may be placed in the closed structure formed by the first display panel 01 and second display panel 02 for exhibition, and correspondingly, the first display panel 01 and second display panel 02 may display related information such as introductory content of the exhibited articles so that the user may view it through the touch control function of the multi-faced display device. When the multi-faced display device is applied to a mobile terminal such as a mobile phone, the first display device and second display device are generally arranged as opaque display panels.

Upon implementation, the first display panel 01 of the multi-faced display device may specifically be a liquid crystal display panel, an organic electroluminescence display panel or an electronic paper display panel. Correspondingly, the second display panel 02 may specifically be a liquid crystal display panel, an organic electroluminescence display panel or an electronic paper display panel.

As the first display panel 01 and second display panel 02 need to be subjected to curving treatment, a flexible substrate needs to be selected to fabricate the first display panel 01 and second display panel 02, and this flexible substrate comprises a glass substrate. In addition, a material of a corresponding functional film layer also needs to have corresponding flexibility to ensure that certain curving treatment may be performed for the first display panel 01 and the second display panel 02.

Figure 3:
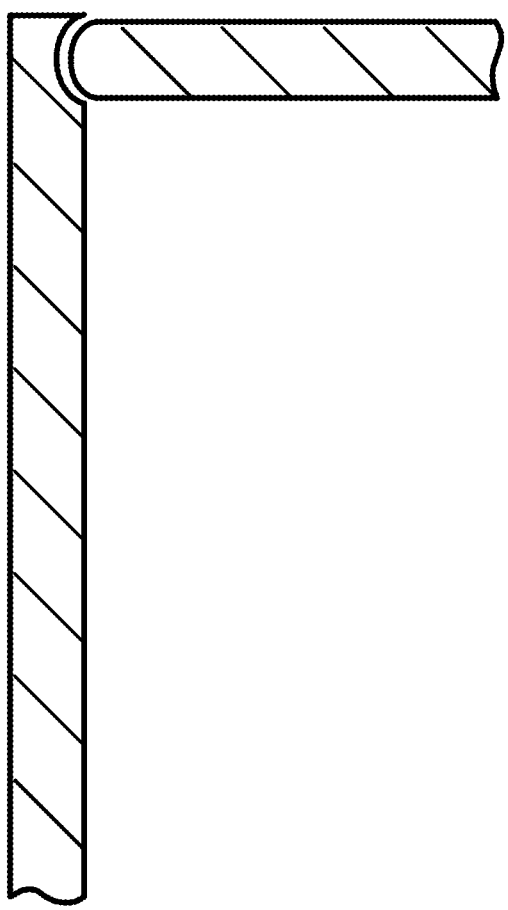
FIG. 3 is a cross-sectional view showing a groove and a corresponding protrusion for assembling two elements.

Upon implementation, in fabricating the multi-faced display device, many assembling manners may be employed between the first display panel 01 and second display panel 02, between the first display panel 01 and the first encapsulating plate 03, between the first display panel 01 and second encapsulating plate 04, between the second display panel 02 and the first encapsulating plate 03, and between the second display panel 02 and the second encapsulating plate 04. Specifically, the assembling manner may be a press-fitting manner via a groove and a corresponding protrusion as shown in FIG. 3, which are engaged with each other, a gluing manner or a screwing manner, and is not limited here.

Encapsulating the first display panel 01 and second display panel 02 by press-fitting or gluing may facilitate use of a bezel-less design at locations of encapsulation at the lateral sides of the first display panel 01 and second display panel 02. For example, in fabricating the first display panel 01 and second display panel 02, the left and right lateral sides thereof may be made bezel-less such that the first display panel 01 and second display panel 02 do not have a bezel at least at locations of encapsulation at the lateral sides.

Figure 4:
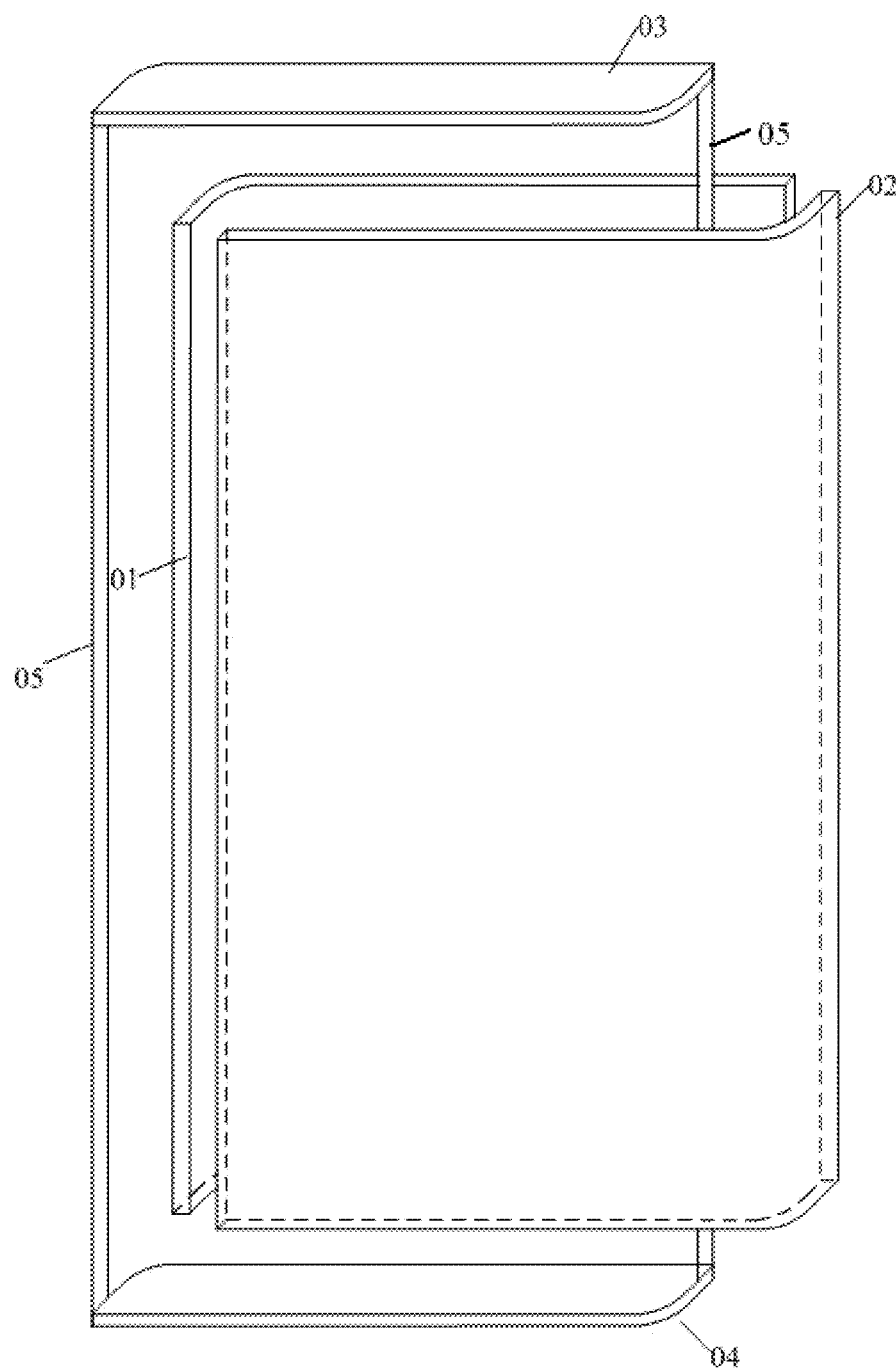
FIG. 4 is a second exploded view showing the structure of parts of a multi-faced display device according to an embodiment of the present disclosure.

With the press-fitting manner or gluing manner being used, wires might be arranged at joints between the first display panel 01 and second display panel 02 so that it becomes difficult to engage the first display panel 01 and second display panel 02 seamlessly. To simplify the encapsulating process, the two lateral sides of the first display panel 01 and second display panel 02 may be respectively encapsulated via a third encapsulating plate 05, as shown in FIG. 4. A circuit may be disposed on the third encapsulating plate 05 to provide a lead wire or interface so as to simplify the process.

Furthermore, the third encapsulating plate 05, the first encapsulating plate 03 and the second encapsulating plate 04 may be of an integral structure so that the integral structure, the first display panel 01 and second display panel 02 may be directly assembled together when the multi-faced display device is assembled.

Generally, the first display panel 01 and second display panel 02 further comprise a circuit board. To ensure connection between the circuit board and a display region of the first display panel 01 and second display panel 02, they both are connected via a flexible electronic skin which generally may be made of a rubber net-like conductive material. When the electronic skin is used to connect the display region with the circuit board, a bezel-less design may be used for all of upper and lower bezels and bezels at locations of encapsulation of lateral sides of the first display panel 01 and second display panel 02 to enable the finally-assembled multi-faced display device to implement truly bezel-less annular display.

Figure 5:
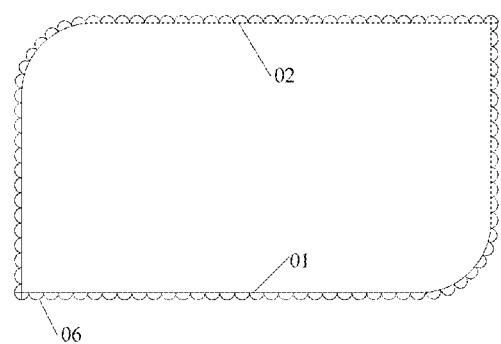
FIG. 5 is a structural schematic view of transparent prism structures of the multi-faced display device according to an embodiment of the present disclosure.

Furthermore, an optical design may be added to the multi-faced display device so that a viewer visually cannot see the encapsulating bezels of the first display panel 01 and second display panel 02. Specifically, as shown in FIG. 5, transparent prism structures 06 for changing a direction of exit light may be fabricated at an encapsulating location of lateral sides of the first display panel 01 and second display panel 02. The transparent prism structures 06 may refract light originally exiting forward at the encapsulating location of the lateral sides of the first display panel 01 and second display panel 02 to the encapsulating location of the lateral sides so that the viewer visually cannot perceive existence of the seam, and visually bezel-less annular display can be achieved.

Noticeably, when the organic electroluminescence display panel is used to fabricate the first display panel and second display panel, thin film encapsulating technology of the organic electroluminescence display panel may be used to achieve a physically bezel-less design. When the liquid crystal display panel or electronic paper display panel is used to fabricate the first display panel or second display panel, the optically bezel-less effect is achieved relying on for example the optical design (i.e., the transparent prism structures) since the encapsulating technology of the liquid crystal display panel or electronic paper display panel cannot achieve true physically bezel-less design. Of course, the bezel-less effect may also be optimized by virtue of for example the optical design when the organic electroluminescence display panel is used to fabricate the first display panel and second display panel.

Upon implementation, the transparent prism structures 06 may be disposed only at the encapsulating location of the lateral sides of the first display panel 01 and second display panel 02. Alternatively, as shown in FIG. 5, the transparent prism structures 06 may also be disposed on all external surfaces of the first display panel 01 and second display panel 02, which will not be limited here.

Figure 6:
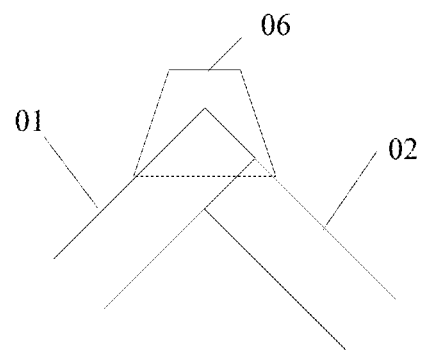
FIG. 6 is a structural schematic view of a transparent prism structure of the multi-faced display device according to an embodiment of the present disclosure.

The transparent prism structures 06 disposed at the encapsulating location of the lateral sides of the first display panel 01 and second display panel 02 should at least partly protrude out of the outside surface of the closed structure, namely, the outside surface of the first display panel 01 and second display panel 02, as shown in FIG. 6. A cross section of the transparent prism structures 06 perpendicular to the outside surface of the closed structure (i.e., the outside surface of the first display panel 01 and second display panel 02) may be set in a shape such as a semi-circular shape as shown in FIG. 5 or an isosceles trapezoid shape as shown in FIG. 6 so as to change the exit direction of the light.

Figure 7:
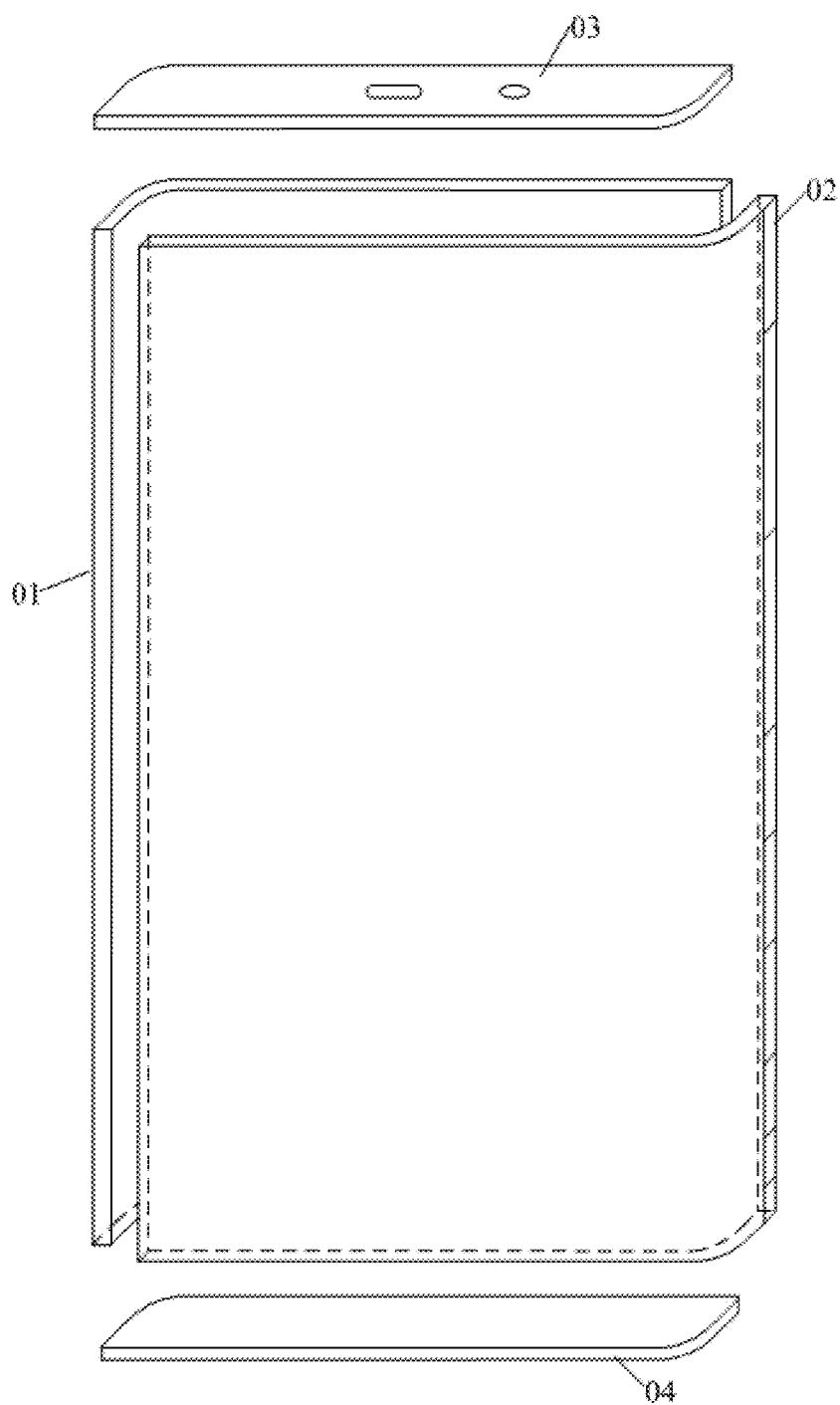
FIG. 7 is a third exploded view showing the structure of parts of a multi-faced display device according to an embodiment of the present disclosure.

In addition, as shown in FIG. 7, the above multi-faced display device provided by the embodiment of the present disclosure may further comprise at least one function slot and/or physical function key. Specifically, the function slot may be an SD card slot, a SIM card slot, a USB insertion slot, an earphone slot, a charging slot and the like; the physical function key may be a switch button, a volume tuning button, a brightness regulating button and the like. When the aforesaid multi-faced display device has a bezel, the above function slot and/or physical function key may be disposed at the encapsulating location of the lateral sides of the first display panel 01 and second display panel 02. Specifically, the function slot and/or physical function key may only be disposed at the encapsulating location of one of the lateral sides, or disposed at the encapsulating location of both of the lateral sides. Alternatively, it may also be disposed at the non-display region of the first display panel 01 and/or second display panel 02. When the aforesaid multi-faced display device according to the embodiment of the present disclosure is bezel-less, the function slot and/or physical function key may be disposed on a surface of the first encapsulating plate 03 and/or the second encapsulating plate 04. FIG. 7 shows two physical function keys disposed on the first encapsulating plate 03, and a plurality of function slots disposed at the encapsulating location of one of lateral sides of the first display panel 01 and second display panel 02.

Furthermore, when the multi-faced display device according to the embodiment of the present disclosure is for example applied to a mobile terminal such as a mobile phone, the multi-faced display device is adapted to display specific information. Since the mobile terminal such as the mobile terminal is associated with personal attributes of the user, the multi-faced display device may be used to display information related to personal attributes of the user in addition to information related to functions (e.g., call, messaging, video playback) of the mobile terminal itself.

Upon implementation, the multi-faced display device according to the embodiment of the present disclosure may comprise a health monitoring unit configured to detect health information of a human body and display corresponding health information (e.g., body temperature, blood sugar value and the like) on the display surfaces of the multi-faced display device. Since such health information is usually only several groups of digits and does not need to occupy a large screen region, it may be displayed using non-main display surfaces of the multi-faced display device. As such, the display region of the main display surface need not be occupied, so the user may monitor the health information while normally viewing other display content on the main display surface. The multi-faced display device according to the embodiment of the present disclosure is advantageous in displaying such health information in that the left side surface or right side surface and the corresponding curved transition surface may be combined into a single non-main display surface enlarge the area of the display area so that such information may also be clearly displayed on the non-main display surface even though the ultra-slim design is employed. This enhances flexibility of product design and user's use experience. Particularly, it is usually desirable to monitor the health information constantly in a long term and maintain the display of the health information. Hence, power may be saved by keeping the non-main display surface displaying the health information on and turning off other display surfaces. Alternatively or additionally, such health information may be displayed on the main display surfaces depending on a location of the health monitoring unit, the user's selection or a specific use environment.

When the multi-faced display device according to the embodiment of the present disclosure has certain bezels, the health monitoring unit may be disposed at the encapsulating location at the lateral side of the first display panel 01 and/or second display panel 02. Specifically, the health monitoring unit may only be disposed at the encapsulating location of one of the lateral sides, or disposed at the encapsulating location of both of the lateral sides. Alternatively, it may also be disposed at the non-display region of the first display panel 01 and/or second display panel 02. When the multi-faced display device according to the embodiment of the present disclosure is bezel-less, the health monitoring unit may be disposed on a surface of the first encapsulating plate 03 and/or the second encapsulating plate 04.

Generally, the health monitoring unit has a data collecting component and a data analyzing and storing component. Specifically, the data collecting component may employ a sensor such as an infrared sensor; the data analyzing and storing component may employ hardware such as a micro controller unit (MCU) and a digital signal processor (DSP). Such hardware has an on-chip storage device for storing program and data. Certainly, an off-chip storage device may also be used as a storing component. In an example, the health monitoring unit may be an infrared detecting unit and/or a minimal invasion detecting unit, wherein the infrared detecting unit is configured to monitor a body temperature and the minimal invasion detecting unit is configured to monitor a blood sugar value. Other types of monitoring units may also be employed for specific objects to be monitored.

Furthermore, when the multi-faced display device according to the embodiment of the present disclosure is applied to an IT display product, a TV set, a mobile phone or the like, an image acquiring means such as a camera and means such as a Blue-tooth means may also be disposed on the non-display regions of the first display panel 01 and/or second display panel 02. This is not for limitation here.

As compared with the multi-faced display device formed by a plurality of planar display panels, the display device according to the embodiment of the present disclosure employs two L-shaped display panels to achieve a curved display surface resulting from connection via arcuate surfaces, thereby enhancing continuity of images displayed in respective directions of the multi-faced display device and providing a capability of displaying specific information in a desired manner.

Apparently, various modifications and variations to the present disclosure may be made by those skilled in the art may make without departing from the spirit and scope of the present disclosure. As such, if such modifications and variations to the present disclosure fall within the scope of claims of the present disclosure and equivalents thereof, the present disclosure is intended to include such modifications and variations.

What is claimed is:

1. A multi-faced display device, comprising: a first display panel curving towards a back side of the first display panel to form an L-shaped structure, the first display panel having a first lateral side edge and a second lateral side edge opposite to the first lateral side edge, and
    a second display panel curving towards a back side of the second display panel to form an L-shaped structure, the second display panel having a first lateral side edge and a second lateral side edge opposite to the first lateral side edge,
    wherein the second lateral side edge and the first lateral side edge of the first display are encapsulated with the first lateral side edge and the second lateral side edge of the second display panel respectively, such that the first and second display panels together form a closed structure,
    wherein each of the L-shaped first and second display panels comprises two straight surface portions and one arcuate portions such that the formed closes structure comprises four straight surface portions and only two arcuate surface portions; and
    wherein at least one selected from the group consisting of an outside surface and an inside surface of the closed structure acts as a display surface of the multi-faced display device;
    wherein a first encapsulating plate for sealing a top of the closed structure and a second encapsulating plate for sealing a bottom of the closed structure.

2. The multi-faced display device according to claim 1, wherein the first display panel and the second display panel, the first display panel and the first encapsulating plate, the first display panel and the second encapsulating plate, the second display panel and the first encapsulating plate, and the second display panel and the second encapsulating plate are assembled via a groove and a corresponding protrusion.

3. The multi-faced display device according to claim 1, wherein the second lateral side edge of the first display panel is encapsulated with the first lateral side edge of the second display panel via a third encapsulating plate, and the first lateral side edge of the first display panel is encapsulated with the second lateral side edge of the second display panel via another third encapsulating plate.

4. The multi-faced display device according to claim 3, wherein the third encapsulating plates, the another third encapsulating plate, the first encapsulating plate and the second encapsulating plate are of an integral structure.

5. The multi-faced display device according to claim 1, further comprising a function structure comprising at least one selected from the group consisting of a slot and a physical key, wherein the function structure is disposed at a position selected from the group consisting of an encapsulating location of the first and second lateral side edges of the first display panel, an encapsulating location of the first and second lateral side edges of the second display panel, a non-display region of the first display panel, a non-display region of the second display panel, a surface of the first encapsulating plate, and a surface of the second encapsulating plate.

6. The multi-faced display device according to claim 1, further comprising a health monitoring unit configured to detect health information of a human body, wherein the health monitoring unit is disposed at a position selected from the group consisting of an encapsulating location of the first and second lateral side edges of the first display panel, an encapsulating location of the first and second lateral side edges of the second display panel, a non-display region of the first display panel, a non-display region of the second display panel, a surface of the first encapsulating plate, and a surface of the second encapsulating plate.

7. The multi-faced display device according to claim 6, wherein the health monitoring unit comprises at least one selected from the croup consisting of an infrared detecting unit and a minimal invasion detecting unit.

8. The multi-faced display device according to claim 6, wherein each of the first display panel and the second display panel comprises a main display surface and a non-main display surface, the non-main display surface being adapted to display the health information detected by the health monitoring unit.

9. The multi-faced display device according to claim 1, wherein the first display panel and the second display panel do not have a bezel at least at an encapsulating location of the first and second lateral side edges.

10. The multi-faced display device according to claim 9, further comprising a circuit board connected to at least one selected from the group consisting of the first display panel and the second display panel via a flexible electronic skin.

11. The multi-faced display device according to claim 9, further comprising a plurality of transparent prism structures provided at least at the encapsulating location of the first and second lateral side edges of the first display panel and the second display panel, each of the transparent prism structures for changing a direction of exit light.

12. The multi-faced display device according to claim 11, wherein each of the plurality of transparent prism structures at least partly protrudes out of the outside surface of the closed structure, a cross section of each transparent prism structure perpendicular to the outside surface of the closed structure being in a semi-circular shape or an isosceles trapezoid shape.

13. The multi-faced display device according to claim 1, wherein the first display panel is a liquid crystal display panel, an organic electroluminescence display panel or an electronic paper display panel, and the second display panel is a liquid crystal display panel, an organic electroluminescence display panel or an electronic paper display panel.

14. The multi-faced display device according to claim 13, wherein the first display panel and the second display panel are touch control display panels.

15. The multi-faced display device according to claim 1, wherein the first display panel is a liquid crystal display panel, an organic electroluminescence display panel or an electronic paper display panel, and the second display panel is a liquid crystal display panel, an organic electroluminescence display panel or an electronic paper display panel.

16. The multi-faced display device according to claim 3, wherein the first display panel is a liquid crystal display panel, an organic electroluminescence display panel or an electronic paper display panel, and the second display panel is a liquid crystal display panel, an organic electroluminescence display panel or an electronic paper display panel.

17. The multi-faced display device according to claim 5, wherein the first display panel is a liquid crystal display panel, an organic electroluminescence display panel or an electronic paper display panel, and the second display panel is a liquid crystal display panel, an organic electroluminescence display panel or an electronic paper display panel.

18. The multi-faced display device according to claim 6, wherein the first display panel is a liquid crystal display panel, an organic electroluminescence display panel or an electronic paper display panel, and the second display panel is a liquid crystal display panel, an organic electroluminescence display panel or an electronic paper display panel.

19. The multi-faced display device according to claim 9, wherein the first display panel is a liquid crystal display panel, an organic electroluminescence display panel or an electronic paper display panel, and the second display panel is a liquid crystal display panel, an organic electroluminescence display panel or an electronic paper display panel.

* * * * *